United States Patent [19]
Hammond et al.

[11] Patent Number: 6,109,918
[45] Date of Patent: Aug. 29, 2000

[54] DENTAL INSTRUMENT HAVING OVERLAPPING HELICAL SCORING PATTERN

[75] Inventors: Neville Hammond, Schaumburg; Michael Haupers, Prospect Heights; Ronald M. Saslow, Chicago, all of Ill.

[73] Assignee: Hu-Friedy Mfg. Co., Inc., Chicago, Ill.

[21] Appl. No.: 09/234,644

[22] Filed: Jan. 21, 1999

[51] Int. Cl.[7] .................................................. A61C 3/00
[52] U.S. Cl. ............................................................ 433/141
[58] Field of Search .................................... 433/127, 141, 433/142, 143, 144, 145, 146, 147, 166; 29/2.25, 417, 557, 558, DIG. 15, DIG. 23, 896.1; 76/101.1, 106, 119

[56] References Cited

U.S. PATENT DOCUMENTS

| | | | |
|---|---|---|---|
| D. 249,062 | 8/1978 | Crafoord et al. | D24/1 D |
| D. 259,660 | 6/1981 | Sosnay | D24/11 |
| D. 394,902 | 6/1998 | Herbst et al. | D24/154 |
| 797,270 | 8/1905 | Dreher | 433/141 |
| 1,314,037 | 8/1919 | Amberg | 29/DIG. 15 |
| 1,503,610 | 8/1924 | Smith | 433/143 |
| 1,723,226 | 8/1929 | Withycombe | 433/147 |
| 2,552,134 | 5/1951 | Berliner | 433/143 |
| 2,818,647 | 1/1958 | Berliner | 433/143 |
| 4,060,897 | 12/1977 | Greenstein | 433/141 |
| 4,759,713 | 7/1988 | Heiss et al. | 433/141 |
| 4,795,344 | 1/1989 | Brewer, Jr. | 433/143 |
| 4,836,781 | 6/1989 | Meinershagen | 433/141 |
| 5,127,833 | 7/1992 | Kline | 433/143 |
| 5,501,597 | 3/1996 | Wilson | 433/141 |
| 5,774,971 | 7/1998 | Manetta et al. | 29/558 |
| 5,816,806 | 10/1998 | Herbst et al. | 433/141 |
| 5,842,267 | 12/1998 | Biederman et al. | 29/558 |

OTHER PUBLICATIONS

Hu–Friedy Colours Dental Instrument Catalog in Dutch, published before filing date of patent application (Jan. 21, 1998).

Advertisement in Dental Products Report Magazine, Apr. 1995.
American Eagle Dental Instrument Catalog, published before filing date of patent application (Jan. 21, 1999).
American Eagle, Promotional Literature received via mail before filing date of patent application (Jan. 21, 1999).
Advertisement in Dental Product Report Magazine, 1996.
Advertisement in RDH Magazine, 1996.
Advertisement in RDH Magazine, Sep. 1996.
Advertisement in RDH Magazine, Oct. 1997.
Patterson Dental Promotional Literature received before filing date of patent application (Jan. 21, 1999).
Promotional Literature received at dental trade show before filing date of patent application (Jan. 21, 1999).
American Eagle Product Catalog, published before filing data of patent application (Jan. 21, 1999).
G. Hartzell & Son Product Catalog, published before filing date of patent application (Jan. 21, 1999).
Nordent, Promotional Literature received via mail before filing date of patent application (Jan. 21, 1999).
Product Brochure, published before filing date of patent application (Jan. 21, 1999).
Advertisement in RDH Magazine, Oct. 1998.

(List continued on next page.)

*Primary Examiner*—Todd E. Manahan
*Attorney, Agent, or Firm*—Rockey, Milnamow & Katz, Ltd.

[57] ABSTRACT

A dental apparatus or instrument includes a hollow, tubular metal handle, closing members fastened to opposite open ends of the handle, and tool parts connected to the closing members. The metal handle includes a central substantially smooth region and two surface contoured regions adjacent to the closing members. The surface contoured regions include wide grooves in a criss-crossed pattern superimposed on V-shaped narrow grooves in a criss-crossed helical pattern. The combination of the two type grooves gives a sure grip feel to the two surface contoured regions. The closing members each include an attachment portion which tightly interfits into an open end of the handle and which is brazed into the handle.

46 Claims, 3 Drawing Sheets

OTHER PUBLICATIONS

Product Literature, published before filing date of patent application (Jan. 21, 1999).

Advertisement in RDH Magazine, Jan. 1999.

Nordent Product Catalog, published before filing date of patent application (Jan. 21, 1999).

Direct Mail Advertisement, published before filing date of patent application (Jan. 21, 1999).

Premier Product Catalog, published before filing date of patent application (Jan. 21, 1999).

Star Product Catalog, published before filing date of patent application (Jan. 21, 1999).

Thompson, Promotional Literature, published before filing date of patent application (Jan. 21, 1999).

Advertisement in Sullivan–Schein Dental Flyer, Oct. 1998.

Thompson Dental Product Catalog, published before filing date of patent application (Jan. 21, 1999).

Patterson Product Catalog, published before filing date of patent application (Jan. 21, 1999).

Sullivan–Schein Dental Catalog, published before filing date of patent application (Jan. 21, 1999).

DENTAL INSTRUMENT HAVING OVERLAPPING HELICAL SCORING PATTERN

FIELD OF THE INVENTION

The present invention relates to dental instruments, particularly hand-held dental instruments having an elongated body with tools carried on one or both ends of the elongated body. Particularly, the invention relates to a hand-held dental instrument having a metal handle with metal tool receptacles on opposite ends thereof for the fixation of tools to the handle.

BACKGROUND OF THE INVENTION

Dental instruments having an elongate metal handle carrying one or two tool parts are known, such as disclosed in U.S. Pat. Nos. 2,818,647 or 4,060,897. U.S. Pat. No. 2,818,647 discloses an instrument having a shank which includes a socket portion which serves as a recessed seat for holding a tool or blade member by a wedge fit. U.S. Pat. No. 4,060,897 discloses a tool having a handle section which threadedly receives a tool section, or the handle section merges into a neck portion which integrally merges into a serrated surface section. The instruments disclosed in these two patents include handle regions having gripping serrations or grooves axially aligned with the handle for enhancing gripping of the instrument.

The present invention recognizes the desirability of providing an instrument handle with an improved gripping surface, and also a handle which can accommodate one or two tool parts into one or both opposite ends, respectively, in a secure and aesthetically pleasing manner.

SUMMARY OF THE INVENTION

The present invention contemplates a dental apparatus which includes a tubular, hollow metal handle having first and second ends with an exterior peripheral surface therebetween. The apparatus includes first and second closing members wherein each member includes an attachment portion. Each of the attachment portions slidably engages a hollow end of the handle and is metallically bonded, without adhesive, to at least one adjacent region of the respective end.

The handle is scored with at least a first single helical grip enhancing pattern. The scoring can exhibit a substantially narrow V-shaped cross section. The scoring is preferably formed with a metal cutting tool having a pointed end.

The handle can also be scored with a second single helical grip enhancing pattern displaced from the first pattern. The scoring of the second pattern can have a substantially rectangular cross section. The second pattern can be formed with a metal cutting tool with a wide, flat end. Preferably, the first and second patterns are each criss-crossed double helical patterns.

Each of the closing members can include a tapered, exterior body portion or cone portion displaced from a respective attachment portion. The attachment portions can each include an undercut region to facilitate bonding with the handle. A brazing compound or paste initially deposited inside the end regions of the handle, flows under capillary action into the undercut regions when melted by heating the instrument in a vacuum oven. The cone portion can include an implement receiving recess.

An implement or tool part can be press fit and/or secured with an adhesive in the implement receiving recess. The adhesive is cured when the instrument is heated in an oven.

Alternatively, a closing member can be attached to one end of the handle, the handle carrying a single tool. The respective other end can be closed by other means such as by an alternate closing member having an end cap. The alternate closing member can have an attachment portion which is formed with the end cap rather than being formed with a cone portion.

According to the invention, a method of manufacturing a dental apparatus is contemplated which includes the steps of: providing an elongated hollow tubular metal stock, providing a glass bead finish on a handle portion of the hollow tubular metal stock, scoring the handle portion first with a first helical grip enhancing pattern, then scoring with a second, displaced helical grip enhancing pattern, and separating the handle portion from the elongated stock by cutting, forming an individual handle.

The first pattern can be scored with a metal cutting tool having a pointed end for providing a scoring with a substantially narrow, V-shaped cross section. The second pattern can be scored with a cutting tool having a flat end, to produce a scoring with a substantially wide, rectangular cross section. Preferably, the first and second patterns are each crisscrossed double helical patterns, formed by axially rotating and passing the tubular stock in forward and reverse direction, along the axis of the tubular stock, against the stationary cutting tools.

After the stock has been cut into individual handles, the closing members can then be assembled into the cut open ends of each of the handles and held there temporarily by a sufficient friction fit or press fit, and then brazed in place. A brazing compound is pre-applied to an inside surface of the handles at ends thereof. The handles are heated to melt the brazing portion to fuse the closing members to each of the handles at the opposite ends thereof.

The present invention provides an effective and cost efficient method of securing implements or tool parts to instrument handles. The closing members can be brazed firmly to the handle providing a reliable and smooth appearing connection thereto. The invention provides a sure gripping surface treatment of the handle portion which increases the ability of the user to make precise manipulations and movements with the instrument.

The invention provides a method of manufacturing a dental apparatus which results in cost effective manufacturing and a reliable article manufactured thereby.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

Figure 1:
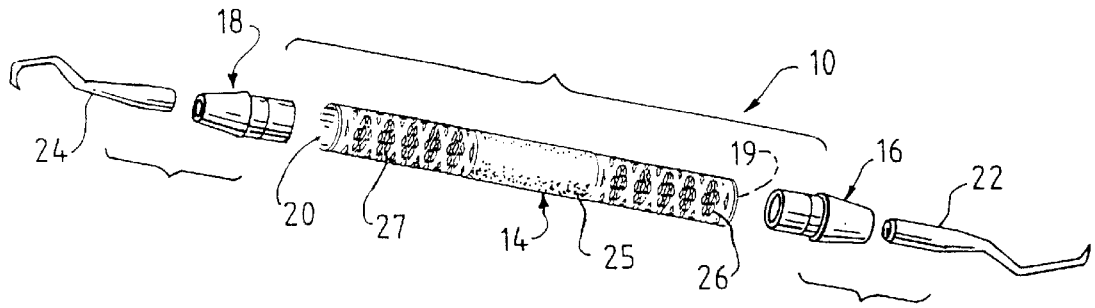
FIG. 1 is an exploded perspective view of a dental apparatus according to the present invention.

While this invention is susceptible of embodiment in many different forms, there are shown in the drawings and will be described herein in detail specific embodiments thereof with the understanding that the present disclosure is to be considered as an exemplification of the principles of the invention and is not intended to limit the invention to the specific embodiments illustrated.

FIG. 1 illustrates a dental apparatus or instrument 10 which includes a handle 14, and two closing members 16, 18 which each partially interfit into one open end 19, 20 of the handle 14. Tool parts or implements 22, 24 are then fixed into the closing members 16, 18 respectively. The handle 14 includes a substantially smooth center section 25 bounded by surface contoured sections 26, 27. Although both the closing members 16, 18 are shown as carrying tool parts, one of the closing members can alternatively include an end cap for merely closing an open end of the handle.

Figure 2:
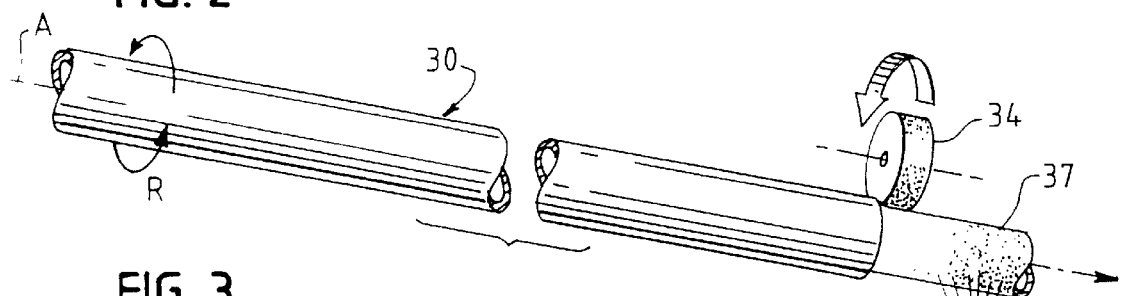
FIG. 2 is a fragmentary perspective view of a first stage of manufacturing of the apparatus shown in FIG. 1.

FIGS. 2 through 7 illustrate manufacturing steps of the dental apparatus. FIG. 2 illustrates the first manufacturing step. An elongate tubular stock 30, typically 12 feet long, and composed of 304 stainless steel, is rotated in a direction R about its axis A and treated by a grinding roll 34, and by a spray nozzle 36 spraying or "blasting" silicon carbide particles. The stock is ground from 0.375" diameter to 0.371" diameter. The silicon carbide used for blasting can be a combination of 60 and 80 grit. The combined action of the grinding roll 34 and the spray nozzle 36 produce a "glass bead" finish on the handle outer surface 37. The tubular stock 30 is then axially advanced in an axial direction A relative to the grinding roll 34 and the spray nozzle 36.

Figure 3:
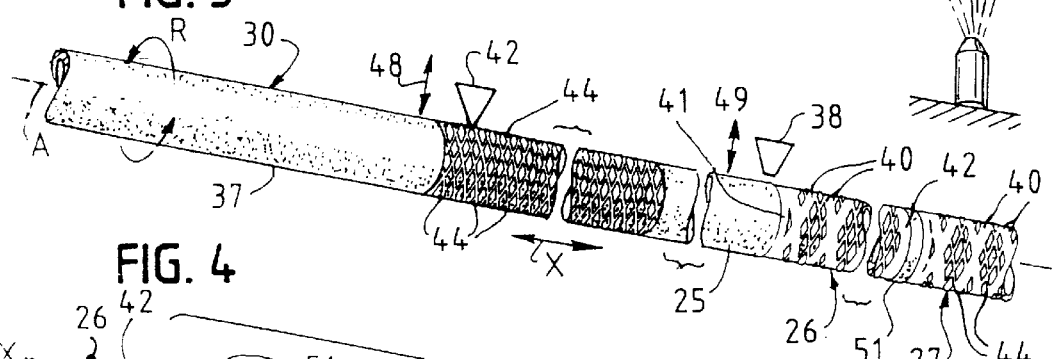
FIG. 3 is a fragmentary perspective view of a second stage of manufacturing of the apparatus of FIG. 1.

FIG. 3 shows the finished surface 37 being further processed downstream of the position shown in FIG. 2, by a flat scoring tool 38 and a pointed scoring tool 42. The stock 30 is axially rotated in the direction R and axially moved in the direction A. The pointed scoring tool 42, being upstream of the flat scoring tool 38 in the direction of advancement A of the stock 30, is engaged to the stock 30 and applies the V-shaped grooves 44 initially within any to-be-contoured surface region 26, 27 during which time the flat scoring tool 38 is disengaged from the stock 30. Next, in sequence, the pointed scoring tool 42 is disengaged from the stock 30, the stock is indexed in the direction A, and the flat scoring tool 38 is engaged to the stock 30.

The flat scoring tool 38 applies the flat wide grooves 40 superimposed over the previously scored region having the previously applied V-shaped grooves 44, to sequentially complete the contouring of each of the regions 26, 27. The scoring tools or cutters 38, 42 are retracted or extended along the radial directions 48, 49 to engage and disengage the stock 30 during the cutting sequences.

The stock 30 is moved along the direction A in forward and reverse directions, during cutting of the V-shaped grooves 44 and during cutting of the wide grooves 40 in order to crisscross the grooves 40, 42, respectively. The stock 30 is moved more slowly in the axial direction A (or the stock rotated more rapidly) during scoring of the V-shaped grooves 44, to cut three times as many grooves 44 as the scoring tool 38 cuts wide grooves 40.

The scoring tool 38 eradicates every third one of the V-shaped grooves 44 when superimposing the wide grooves 40 on the regions 26, 27. The scoring tools 38, 42 may make several passes in reverse directions across each region 26, 27 to make grooves 40, 44 of the desired depth. The grooves are preferably cut 0.004 to 0.006 inches deep. The wide grooves 40 can be about 0.041 inches wide. The narrow grooves 44 can be about 0.015 inches wide at the surface and about 0.013 inches wide at the groove bottom. The scoring tools thus provide two displaced double helical scoring patterns, one comprised of narrow grooves and one comprised of wide grooves. At the end of each region 26, 27 a non-helical axially oriented band 41, 42 respectively is cut, continuous with the wide grooves 40.

After the regions 26, 27 have been scored with both style grooves 40, 44 the stock 30 indexes a distance approximately equal to the length of one handle 14, to begin scoring on two new spaced apart regions 26, 27 with the scoring tools 38, 40. As illustrated in FIG. 3 the scoring between the adjacent regions 26, 27 is spaced by a gap 51. The stock 30 retains the glass bead surface in this gap 51.

Figure 4:
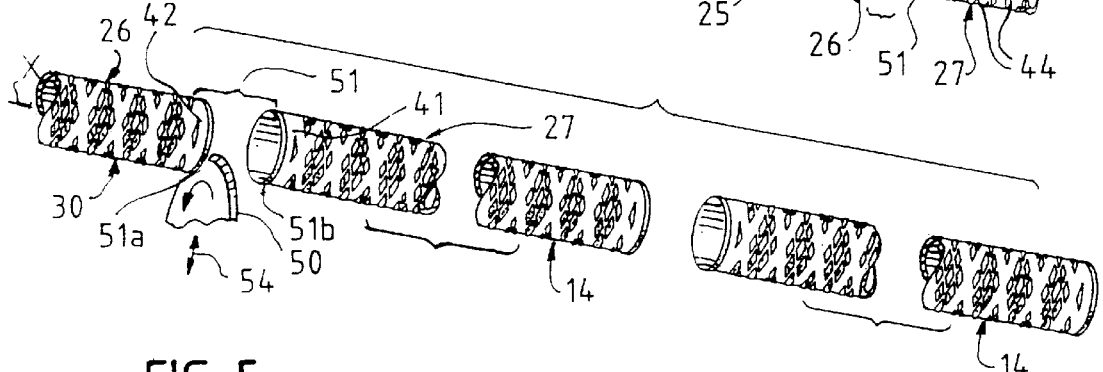
FIG. 4 is a fragmentary perspective view of a third stage of manufacturing of the apparatus of FIG. 1.

FIG. 4 illustrates a handle cutting step using a rotary cutter 50 movable in the radial direction 54 to separate finished handles 14 from the stock 30. The cutter is located downstream of the scoring tools 38, 42 shown in FIG. 3. The stock 30 is cut at a midpoint of the gap 51, leaving bands 51a, 51b on the adjacent regions 26, 27. After the handles are separated, a brazing compound or paste 68 is applied into each open end 19, 20 of each handle.

Figure 5:
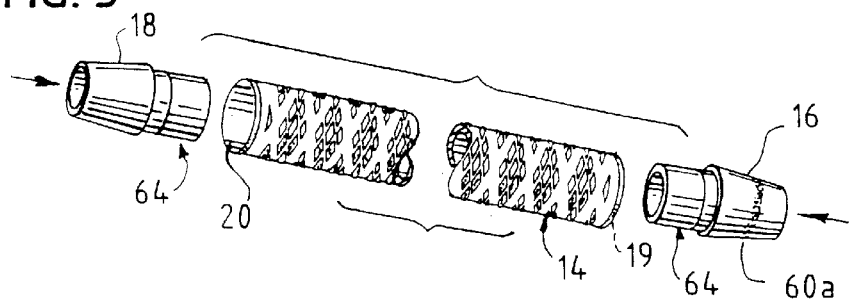
FIG. 5 is an exploded perspective view of a fourth stage of manufacturing of the apparatus of FIG. 1.

FIG. 5 illustrates the next step in the manufacturing process wherein the closing members 16, 18 are press fit into open ends 19, 20 of the handle 14, respectively. The closing members 16,18 have attachment portions 64 which have base diameters sized to be substantially press fit or frictionally fit into the open ends 19, 20 as described below with regard to FIG. 6.

Figure 6:
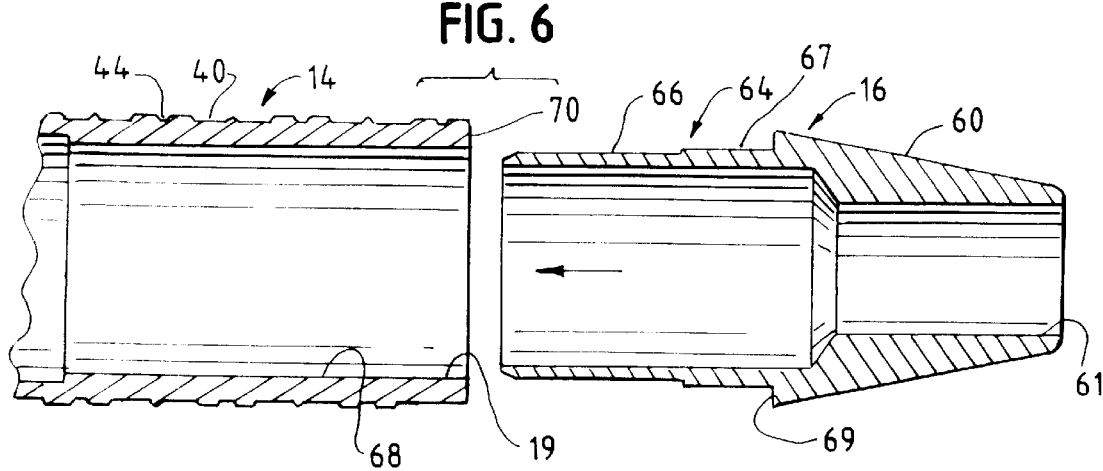
FIG. 6 is an enlarged fragmentary sectional view of a portion of the apparatus of FIG. 1.
Figure 8:
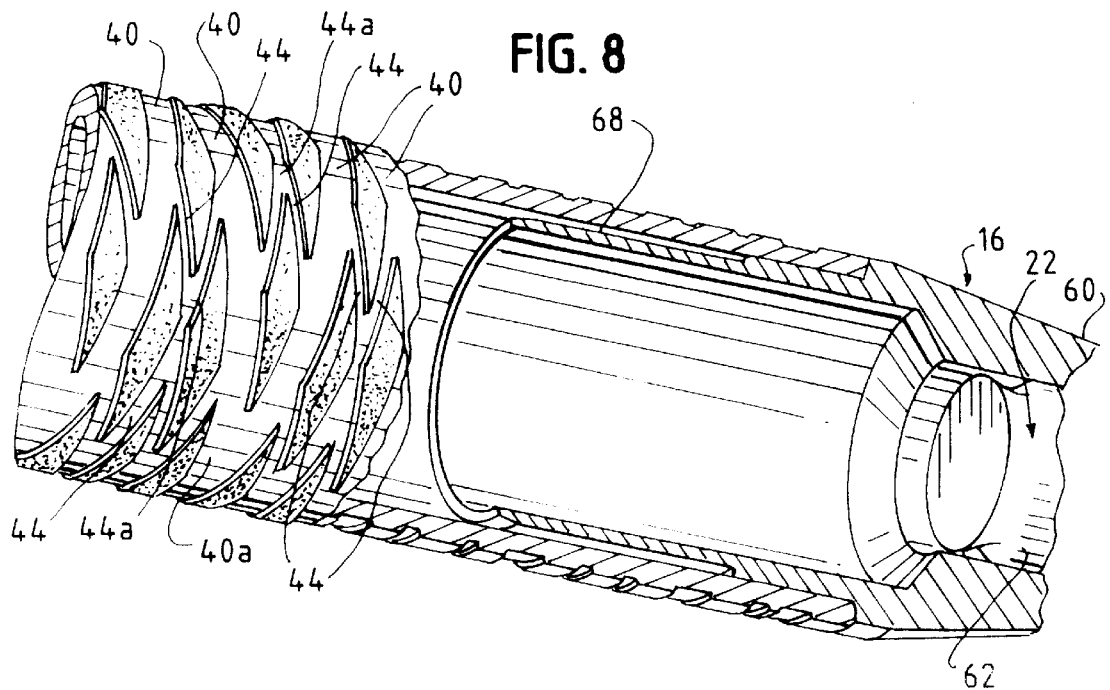
FIG. 8 is an enlarged fragmentary perspective view of a portion of the apparatus of FIG. 1.

As shown in FIG. 6, the closing member 16, typical of both closing members 16, 18 includes a tool-receiving body portion 60. The tool-receiving body portion 60 is substantially frustoconical in shape and has a tool-receiving port 61 for receiving a shank end 62 of a tool 22 (as shown in FIG. 8). The body portion 60 can have a band 60a of surface contouring, such as knurling, for improved gripping on the body portion, as shown in FIG. 5.

Alternatively, for a single tool instrument, one of the closing members 16, 18 can have an end cap (not shown) instead of a tool-receiving body portion, for merely closing one open end 19, 20 of the handle.

The closing member 16 includes the attachment portion 64 depending from the tool-receiving body portion 60. Attachment portion 64 interfits into the open end 19 until a shoulder 69 abuts an end surface 70 of the handle 14. The attachment portion 64 includes an undercut end region 66 adjacent a somewhat thicker base region 67. The base region 67 has an outside diameter slightly larger than an inside diameter of the open end 19 to facilitate a press fit between the attachment portion 64 and the handle 14. The brazing compound 68 is pre-applied to an inside of the handle at the open ends 19, 20. When melted by heating, the compound 68 flows by capillary action into the undercut region 66 and when cooled, the brazing compound 68 joins the closing members 16, 18 to the handle 14.

Figure 7:
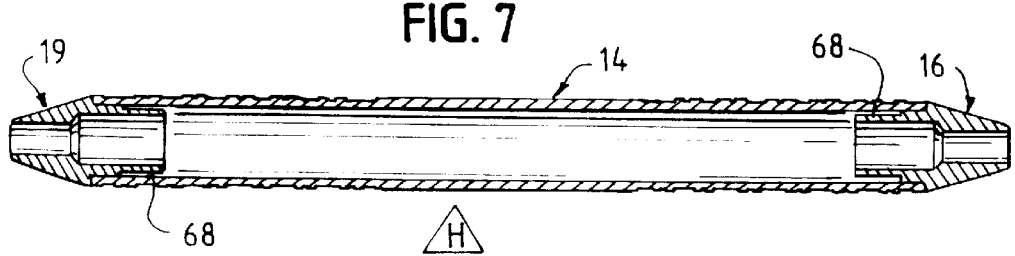
FIG. 7 is a sectional view of a fifth stage of manufacturing of the apparatus of FIG. 1.

As shown in FIG. 7, a heat supply indicated schematically as "H" is then applied to the handle and attachment portions to melt the brazing compound 68 and firmly join the closing members 16, 18 to the handle 14. The heat supply is advantageously provided by a vacuum oven to prevent discoloration of the instrument 10. The heat supply can also be provided by another suitable heat source.

As illustrated in FIG. 8, a tool part 22 is then press fit into the tool-receiving port 61 of the closing member 16. The tool part 24 is fit in substantially identical fashion to the closing member 18. The tool shank 62 is frictionally held within the tool-receiving body portion 60. An adhesive can be used between the tool-receiving aperture 61 and the tool shank 62 to additionally secure the tool part. The adhesive can be cured in the vacuum oven during the brazing operation.

Figure 9:
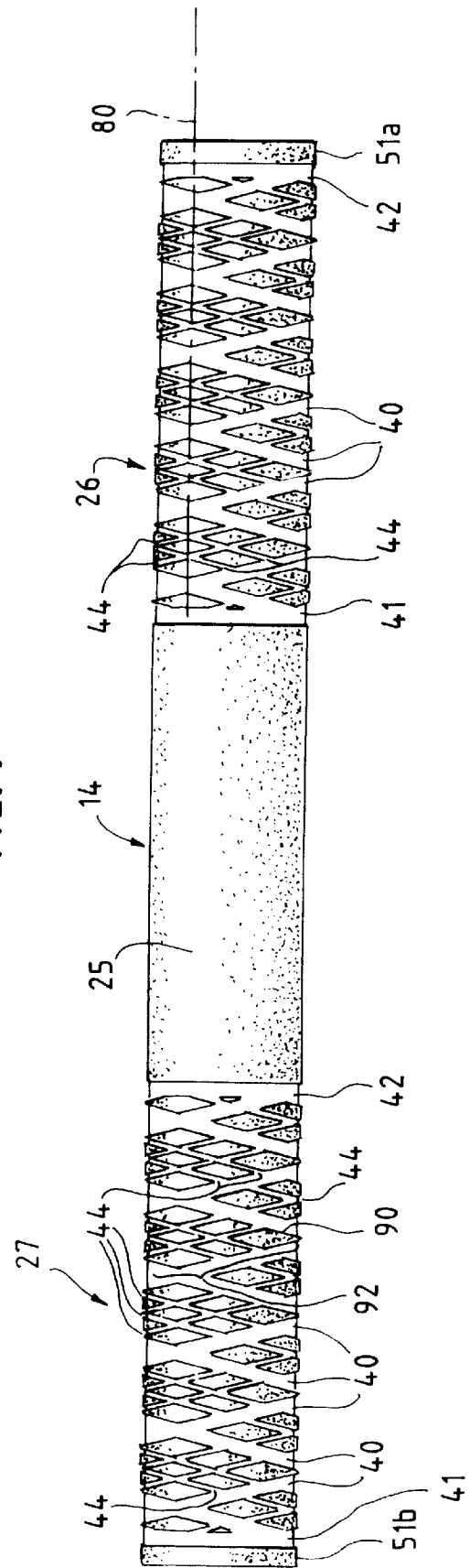
FIG. 9 is an enlarged elevational view of the handle shown in FIG. 4.

As illustrated in FIGS. 8 and 9, the narrow grooves 44 intersect each other at first positions 44a. The wide grooves intersect each other at second positions 40a. In the finished product, across a reference line 80 shown in FIG. 9, there are two first positions 44a between each adjacent second positions 40a. In the finished product there are approximately twice the amount of narrow grooves 44 as wide grooves 40, as illustrated in FIG. 9.

As shown in FIG. 9, the application of crisscrossed wide grooves 40 and narrow grooves 44 creates a pattern of raised small triangles 90 which are themselves grouped into triangle group patterns 92. The patterns 92 provide a sure grip and feed for the user manipulating the handle 14 to work the tool parts 22, 24 with precision, in a non-slip secure manner.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A dental apparatus, comprising:
    a tubular, hollow metal handle with first and second ends and an exterior peripheral surface therebetween wherein first and second, different, helical scoring patterns are cut into the handle,
    first and second closing members wherein each closing member includes a body portion and an attachment portion, wherein each of the attachment portions slidably engages a respective hollow end of the handle and wherein the attachment portions are metallically bonded, without adhesive, to at least one adjacent region of the respective end.

2. An apparatus as in claim 1 wherein the first scoring pattern exhibits a substantially rectangular cross section.

3. An apparatus as in claim 2 wherein the second scoring pattern exhibits a substantially V-shaped cross section.

4. An apparatus as in claim 3, wherein said first and second scorings have constant cross sections and said first scoring has a larger cross section than said second scoring.

5.. An apparatus as in claim 1, wherein said first and second patterns are applied to two spaced apart regions adjacent to said closing members, and a relatively smooth region is provided between the spaced apart regions.

6. An apparatus as in claim 1 wherein the attachment portions each include an undercut region for facilitating bonding with the handle.

7. An apparatus as in claim 1 wherein at least one of the closing members includes a tapered exterior portion displaced from a respective attachment portion.

8. An apparatus as in claim 7 wherein the tapered portion includes a tool-receiving recess.

9. An apparatus as in claim 8 which includes a tool slidably received in the recess.

10. A device as in claim 1 wherein the first and second helical scoring patterns are double helical patterns.

11. A device as in claim 10 wherein the first helical pattern has first pitch and the second helical pattern has a second, different pitch.

12. A device as in claim 1 wherein the first helical pattern has first pitch and the second helical pattern has a second, different pitch.

13. A method of manufacturing a dental instrument comprising the steps of:
    providing an elongate tubular stock;
    grinding the outside surface of the tubular stock and applying a sprayed silicon carbide treatment:
    scoring an outside surface of the tubular stock by crisscrossed wide flat grooves and by crisscrossed narrow grooves; and
    cutting off individual lengths of the tubular stock to form handles.

14. A method according to claim 13 providing the further steps of:
    providing for each handle two closing members each having an attachment portion for being inserted into open ends of each handle, and a tool-receiving recess;
    brazing an attachment portion into the open ends of each handle and heating the handle.

15. A method according to claim 13, wherein said step of scoring is further defined in that the crisscrossed wide grooves are intersecting at positions alternately with intersecting positions of the narrow grooves.

16. A method of manufacturing a dental instrument comprising the steps of:
    providing an elongate tubular stock;
    grinding the outside surface of the tubular stock and applying a sprayed silicon carbide treatment;
    scoring an outside surface of the tubular stock;
    cutting off individual lengths of the tubular stock to form handles;
    providing for each handle at least one closing member having an attachment portion for insertion into an open end of each handle, and a tool-receiving recess;
    applying brazing compound to an inside surface of each handle adjacent said open end; and
    inserting an attachment portion into the open end of said handle and heating the handle to melt the brazing compound.

17. A method according to claim 16, wherein said step of scoring is further defined in that the handle surface is scored by crisscrossed wide flat grooves and is scored by crisscrossed narrow grooves.

18. A method according to claim 16, wherein said step of scoring is further defined in that the crisscrossed wide grooves are intersecting at positions alternately with intersecting positions of the narrow grooves.

19. A method according to claim 16 comprising the further step of fitting a tool part into each tool-receiving recess.

20. A dental device comprising:
    an elongated handle having first and second ends and an exterior peripheral surface therebetween;
    first and second different helical scorings in at least a portion of the peripheral surface wherein the scorings have a same depth.

21. A dental apparatus, comprising:
    a tubular, metal handle with first and second ends and an exterior peripheral surface therebetween;
    at least one tool part mounted to one of said first and second ends;
    wherein said peripheral surface of said handle has at least one region having a first scoring forming a first helical scoring patterns, and a second scoring forming a second displaced helical scoring pattern, said first scoring pattern having a substantially wider cross section than said second scoring pattern, said first scoring pattern overlapping said second scoring pattern within said one region.

22. A dental apparatus according to claim 21, wherein said first and second patterns are each crisscrossed double helical patterns.

23. A dental apparatus according to claim 22, wherein said first scoring intersects itself at first positions between second positions where said second scoring intersects itself.

24. A dental apparatus according to claim 21 wherein said first and second patterns are applied in spaced apart regions adjacent to said first and second ends, and said peripheral surface is substantially smooth in a central region between said spaced apart regions.

25. A handle for a dental instrument, comprising:

a tubular, metal handle with first and second ends and an exterior peripheral surface therebetween;

wherein said peripheral surface of said handle has at least one region having a first scoring forming a first helical scoring pattern with a first pitch, and a second scoring forming a second, displaced, helical scoring pattern of a second, different, pitch, said first scoring having a substantially wider cross section than said second scoring.

26. A dental apparatus according to claim 25, wherein said first and second patterns are each crisscrossed double helical patterns.

27. A dental apparatus according to claim 26, wherein said first scoring intersects itself at first positions between second positions where said second scoring intersects itself.

28. A dental apparatus according to claim 25 wherein said first and second patterns are applied in spaced apart regions adjacent to said first and second ends, and said peripheral surface is substantially smooth in a central region between said spaced apart regions.

29. A dental device comprising:

an elongated handle having first and second ends and an exterior peripheral surface therebetween;

first and second different overlapping helical scorings in at least a portion of the peripheral surface wherein the scorings exhibit first and second different numbers of scores per unit length of the handle.

30. A device as in claim 29 wherein the handle is tubular.

31. A device as in claim 29 wherein the first scoring exhibits on the order of three times the grooves of the second scoring.

32. A device as in claim 29 wherein the scorings have different cross sections.

33. A device as in claim 32 wherein one cross section is wider than the other.

34. A device as in claim 29 wherein one cross section is generally rectangular and the other is V-shaped.

35. A dental device comprising:

an elongated handle having first and second ends and an exterior peripheral surface therebetween;

first and second different helical scorings in at least a portion of the peripheral surface wherein the scorings form spaced-apart diamond shapes separated by a peripheral surface of a substantially constant radius.

36. A device as in claim 35, wherein said spaced-apart diamond shapes are grouped to form diamond-shaped groups that are spaced apart by a wider peripheral surface of a substantially constant radius.

37. A dental apparatus, comprising:

a tubular, hollow metal handle with first and second ends and an exterior peripheral surface therebetween wherein first and second, different, helical scoring patterns are cut into the handle;

a closing member that includes a body portion and an attachment portion, wherein said attachment portion slidably engages a respective hollow end of the handle and wherein the attachment portion is metalically bonded, without adhesive, to an adjacent region of the respective end.

38. An apparatus as in claim 37, wherein the first scoring pattern is formed by a first scoring being substantially rectangular in cross section.

39. An apparatus as in claim 38, wherein the second scoring pattern is formed by a second scoring being substantially triangular in cross section.

40. An apparatus as in claim 39, wherein said first and second scorings have constant cross sections and said first scoring has a larger cross section than said second scoring.

41. An apparatus as in claim 37, wherein said patterns are overlapping.

42. An apparatus as in claim 37, wherein said patterns have different numbers of scores per unit length of the handle.

43. An apparatus as in claim 37, wherein said scoring patterns are each double helical scoring patterns.

44. An apparatus as in claim 43, wherein said first and second scoring patterns are formed by first and second scorings respectively, and said first scoring is wider in cross section than said second scoring.

45. An apparatus as in claim 37, wherein said first and second scoring patterns are formed by first and second scorings respectively, said first scoring having a wider cross section than said second scoring and said second scoring having more turns per unit length of the handle than said first scoring.

46. An apparatus as in claim 1, wherein said first and second scoring patterns are formed by first and second scorings respectively that have constant cross sections, and said first scoring has a larger cross section than said second scoring, and said first and second patterns are each double helical patterns.

* * * * *